(12) United States Patent
Fung et al.

(10) Patent No.: US 7,057,111 B2
(45) Date of Patent: Jun. 6, 2006

(54) CABLE ASSEMBLY FOR ELECTROSURGICAL PENCIL

(76) Inventors: Alex Fung, 35 Tel Lin Pal Road, Kwai Chung, New Territories, Hong Kong (CN); Kipson Fung, 35 Tai Lin Pai Road, Kwai Chung, New Territories, Hong Kong (CN)

( * ) Notice: Subject to any disclaimer, the term of this patent is extended or adjusted under 35 U.S.C. 154(b) by 0 days.

(21) Appl. No.: 10/802,320

(22) Filed: Mar. 16, 2004

(65) Prior Publication Data

US 2005/0205288 A1     Sep. 22, 2005

(51) Int. Cl.
*H02G 15/02* (2006.01)

(52) U.S. Cl. .................................. 174/74 R

(58) Field of Classification Search ............ 174/113 R, 174/74 R; 439/606, 660, 693, 930, 825, 439/827, 592, 600
See application file for complete search history.

(56) References Cited

U.S. PATENT DOCUMENTS

| | | | | |
|---|---|---|---|---|
| 4,834,677 A | * | 5/1989 | Archang | 439/660 |
| 5,674,095 A | * | 10/1997 | Tanhehco et al. | 439/731 |
| 5,993,256 A | * | 11/1999 | Shimojyo | 439/604 |
| 6,142,824 A | * | 11/2000 | Savoca et al. | 439/531 |
| 6,146,211 A | * | 11/2000 | Okamoto et al. | 439/693 |
| 6,297,455 B1 | * | 10/2001 | Wijnberg et al. | 174/113 R |
| 2005/0124200 A1 | * | 6/2005 | Nudd et al. | 439/346 |

FOREIGN PATENT DOCUMENTS

JP     2002-245860     * 8/2002

* cited by examiner

*Primary Examiner*—Chau N. Nguyen
(74) *Attorney, Agent, or Firm*—Alix, Yale & Ristas, LLP

(57) ABSTRACT

A cable assembly for an electrosurgical pencil comprises a power and signal transmitting multiple-core cable with an attachment plug, in which the power transmitting core has more conductors and thicker insulation than the two signal transmitting cores. The attachment plug has plastic plug-pins with spring-steel strips, or has metal plug-pins with recesses on the plug body near the plug-pins, to increase the flexibility to mate with any loose or tight socket. The cable assembly of this invention is cheaper in cost, lighter in weight, thinner in outside diameter, more flexible in total length and provides a more stable plug-socket connection.

16 Claims, 5 Drawing Sheets

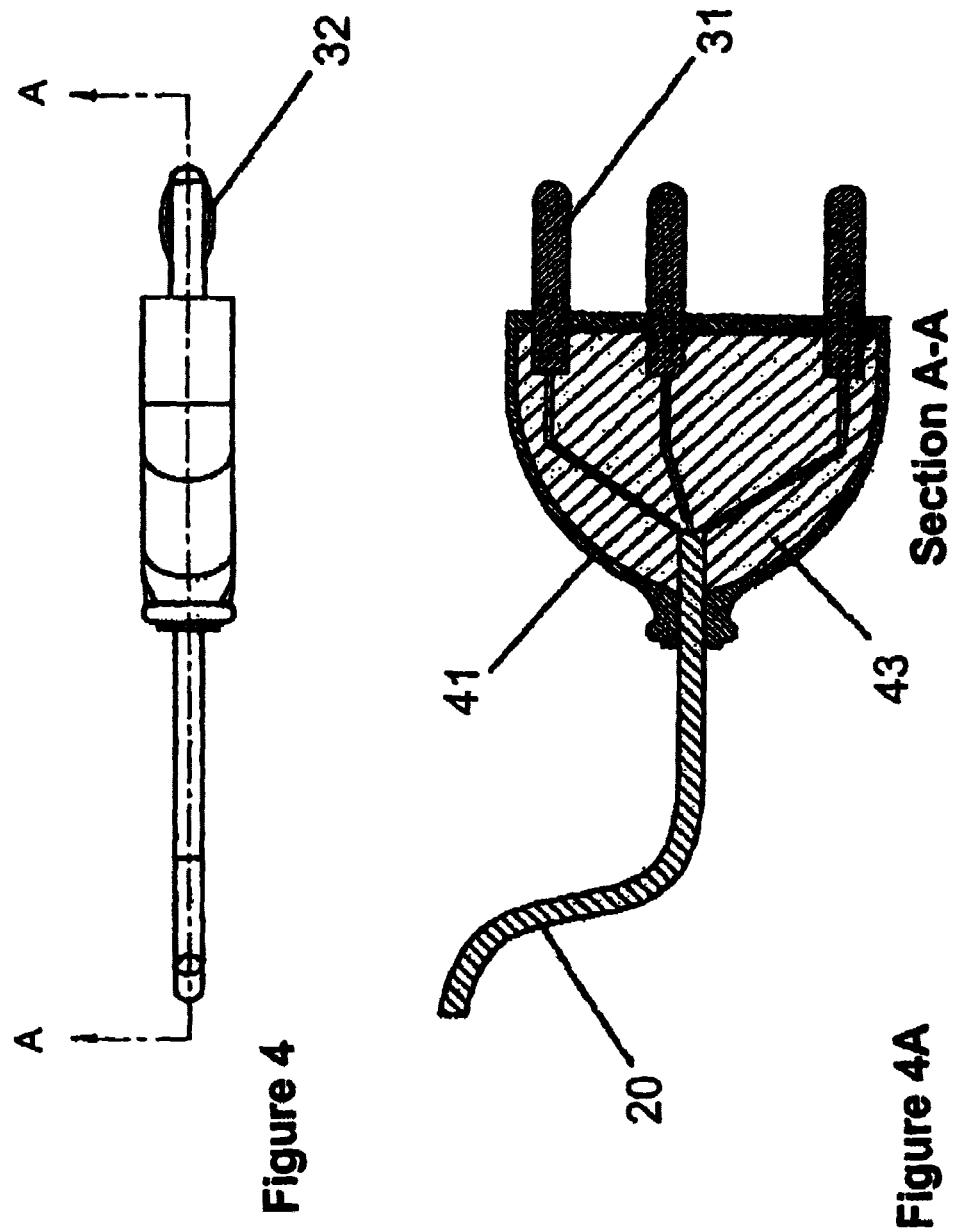

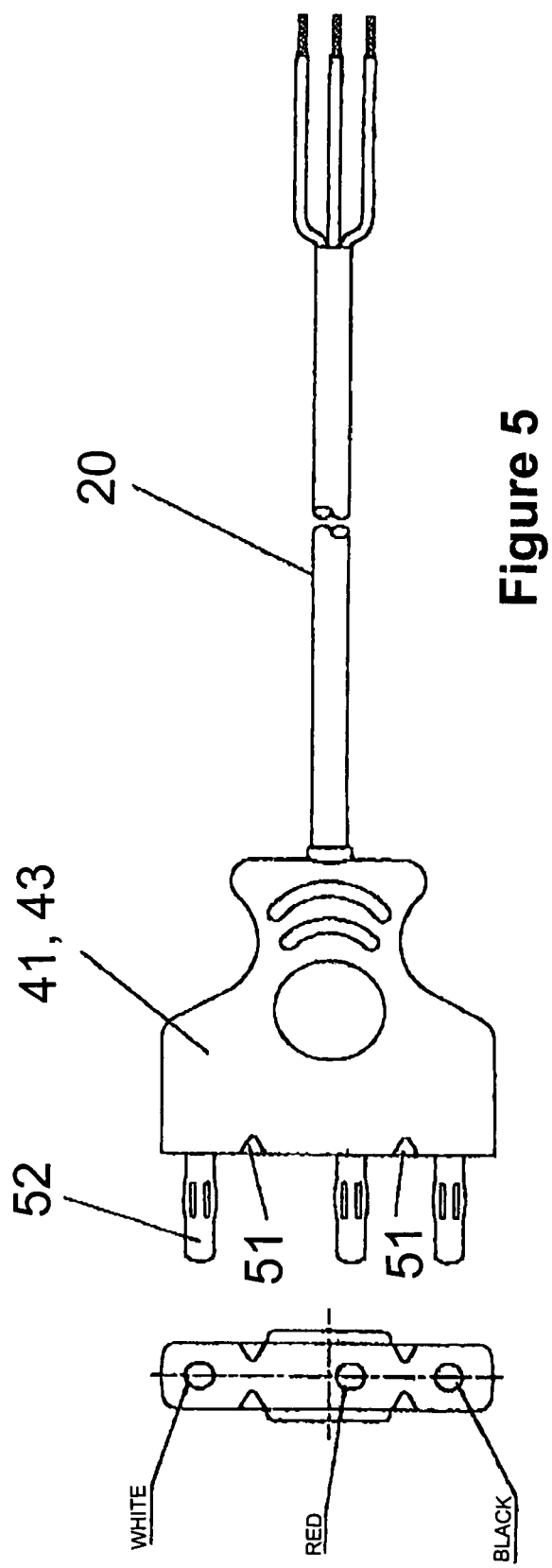
Figure 5
Figure 5A
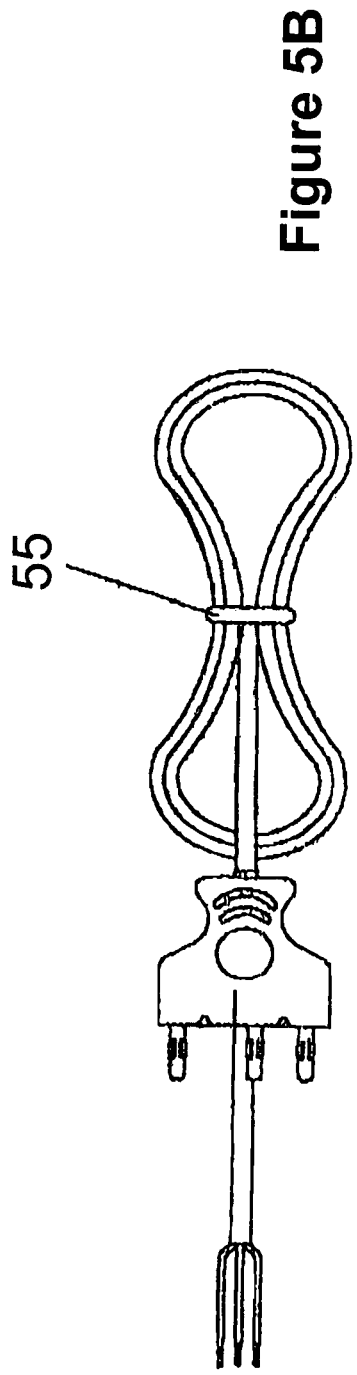
Figure 5B

CABLE ASSEMBLY FOR ELECTROSURGICAL PENCIL

FIELD OF THE INVENTION

This invention relates to a cable assembly, particularly to a cable assembly used for an electrosurgical pencil.

BACKGROUND OF THE INVENTION

The cable assembly used for an electrosurgical pencil includes a cable and a attachment plug. Until now, all manufacturers of electrosurgical pencils have paid little attention to the cable assembly. They typically have purchased existing traditional general-use three-core cables with an existing attachment plug to equip their electrosurgical pencils.

As for the cable, a three-core cable for general-use must have three cores in the same conductor diameter and same insulation, while in an electrosurgical pencil, only one core is used for transmitting heavy power and the other two are only used for transmitting signals. Therefore, the conductor diameter and insulation of the other two cores can be greatly reduced. To do so, not only the cost can be reduced, but also the operational function of the cable can be raised. For example, the main core of said three cores can still meet the test according to AAMI standard. Therefore, the conductor diameter should be AWG#26 (or 7×0.16 mm strands) and the insulation thickness will be thicker. Since the other two cores are only used for transmitting signals, only AWG#28 (or 4×0.16 mm strands) will be enough. The general-use cable will be more expensive, rigid and heavy than the Safety Standard (AAMI) required. If the cable is made per the actual requirements, the cable will be thinner in outside diameter and cheaper in cost. Besides, it will be lighter in weight and more flexible than the traditional general-use cable. This may help to enhance the precision of a surgical operation.

As for the attachment plug of the cable for an electrosurgical pencil, since the traditional attachment plug is designed only per Safety Standard (AAMI), the practicality of the surgical operation was conventionally not considered. For example, in safety testing, each of three cores should be tested with strong current under high voltage, and testing focuses on the temperature-rise, insulation break-down, etc. In any power transmitting case, since the current is strong and the voltage is high, the contacting requirement is low. Even if the contact between the plug-pins and the socket is bad, there will be only an interruption of the current transferring and no safety problem will take place. By contrast in the electrosurgical pencil, since the two cores are transmitting signals, no strong current and high voltage are used; therefore, the contact between the plug-pins and socket must be more sensitive than in safety testing. If the contact between the plug and the socket is unstable and the signal transmitting is interrupted, though there is no safety problem to the device, there may be a terrible safety problem to the patient during the operation. Therefore, the traditional attachment plug is not ideal to use in different electrosurgical generators. For example, plug-pins used to transmit signals should be more sensitive than plug-pins used to transmit power supplies. Simply speaking, the attachment plug used for power transmitting can not meet the requirement of transmitting stable signals.

Furthermore, if the plug-pins are too loose to plug in, they will easily pull out during the operation. If they are too hard to plug in, they will be too difficult to use.

SUMMARY OF THE INVENTION

An object of this invention is to provide a cable assembly for an electrosurgical pencil which overcomes certain prior art deficiencies such that, in comparison to certain conventional cable assemblies, the cable assembly of this invention is cheaper in cost, lighter in weight, thinner in outside diameter, more flexible in total length, and/or provides a more stable plug-socket connection.

For achieving the above mentioned object, the cable assembly of this invention comprises a power and signal transmitting multiple-core cable with an attachment plug, in which the power transmitting core has more conductors and thicker insulation than two signal transmitting cores. The attachment plug has plastic plug-pins with spring-steel strips, or has metal plug-pins with recesses on the plug body near the plug-pins, for increasing the flexibility to any loose or tight socket in mating.

BRIEF DESCRIPTION OF THE DRAWINGS

FIG. 4 is a side view of the attachment plug.
FIG. 4A is a section view of the attachment plug of this invention taken along the line A—A of FIG. 4.
FIG. 5 is a plan view, partly broken away, of the cable assembly of this invention.
FIG. 5A is an end view of the cable assembly of FIG. 5.
FIG. 5B is a plan view of the cable assembly of FIG. 5 with the cable in a coiled form.

DETAILED DESCRIPTION OF THE PREFERRED EMBODIMENTS

Figure 1:
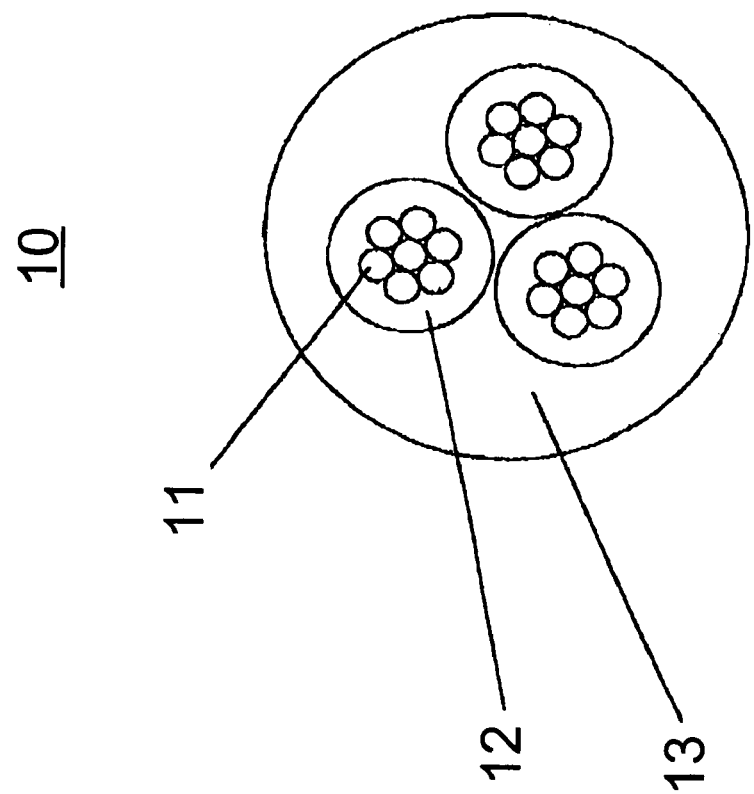
FIG. 1 is a section view of prior art general-use cable.

FIG. 1 is a section view of a prior art general-use power transmitting cable 10. There are three cores in the cable 10. Each core includes a strand of 7 conductors 11 and an insulation coat 12. An outer sleeve 13 encloses the three cores to form an integrated cable 10. Since in safety testing, each core must be tested under same the ampere/voltage/wattage rating, the three cores must have the same construction. This will reduce the flexibility of the cable in operation.

Figure 2:
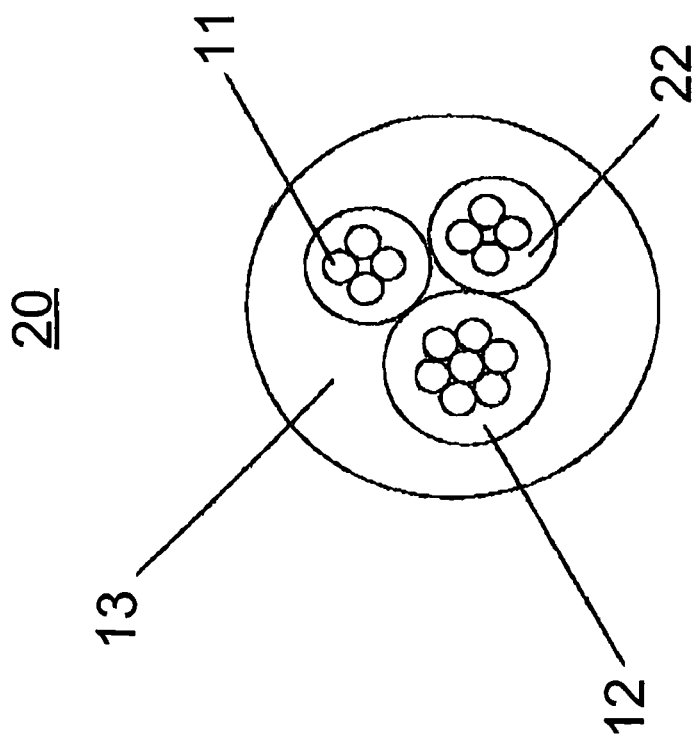
FIG. 2 is a section view of the cable of this invention.

FIG. 2 is a section view of the cable of this invention. In FIG. 2, the cable of this invention is designated by the numeral 20. In cable 20 there still are three cores. The core used for transmitting power is substantially the same one shown in FIG. 1. For the other two cores, since they are used to transmit signals, the number of conductors is reduced to 4. Thus, the total number of the conductors in a given cable is reduced to 15. It is almost a 50% reduction in comparison to FIG. 1. Because in FIG. 2, the two cores are transmitting signals, it is not necessary to transmit large current. Therefore, the flexibility of the cable 20 will be increased at least 50% over that of the cable 10. In addition, the outer diameter of the whole cable will be reduced 20%. Therefore, the cable 20 is thinner, lighter, and more flexible than cable 10. The cost of the cable 20 will be accordingly greatly reduced over cable 10 by virtue of the copper and insulation materials saved.

Figure 3:
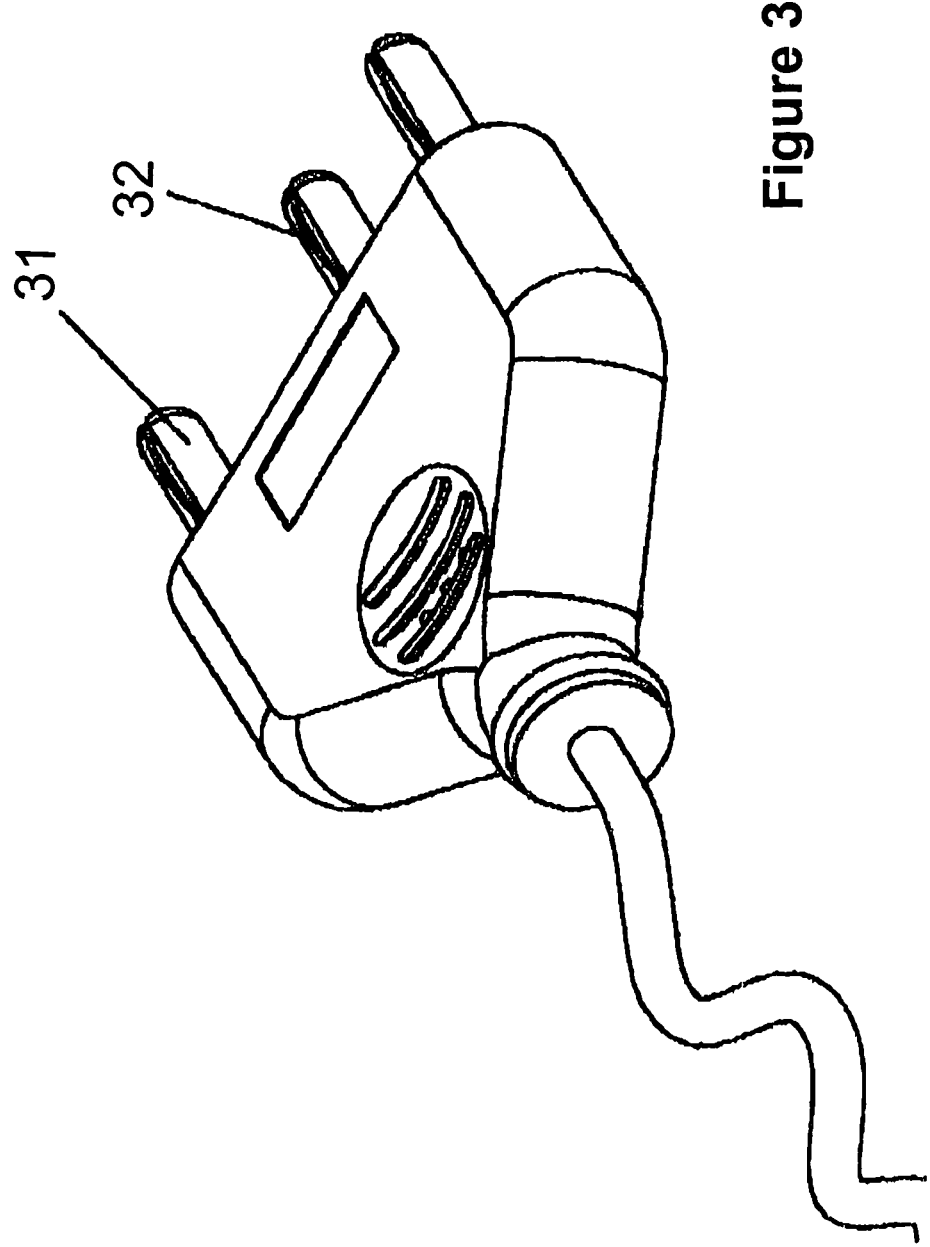
FIG. 3 is a perspective view of the attachment plug of this invention.

FIG. 3 is a perspective view of the attachment plug of this invention. The plug-pins 31 in FIG. 3 are made of plastics. Therefore, spring strips 32 made of spring steel should be used to transmit electricity. In this embodiment, each plug-pin 31 has two oppositely located spring-steel strips 32.

FIGS. 4 and 4A are respectively side and a section view of FIG. 3. In FIGS. 4 and 4A, the attachment plug 30 comprises a plastic outer mould 41, three plastic plug-pins 31, and the cable 20. Since the plug-pins 31, the outer mould 41 and inner mould 43 all are made of plastics, the flexibility of plug-pins 31 is good. This will cause all plug-pins to be easily inserted into any loose or tight socket. In FIG. 4A, the three cores are shown embedded in the gutters of the inner mould 43 for avoiding contact with each other and all three strands are soldered to (not shown) the spring strips 32, respectively.

Figure 4B:
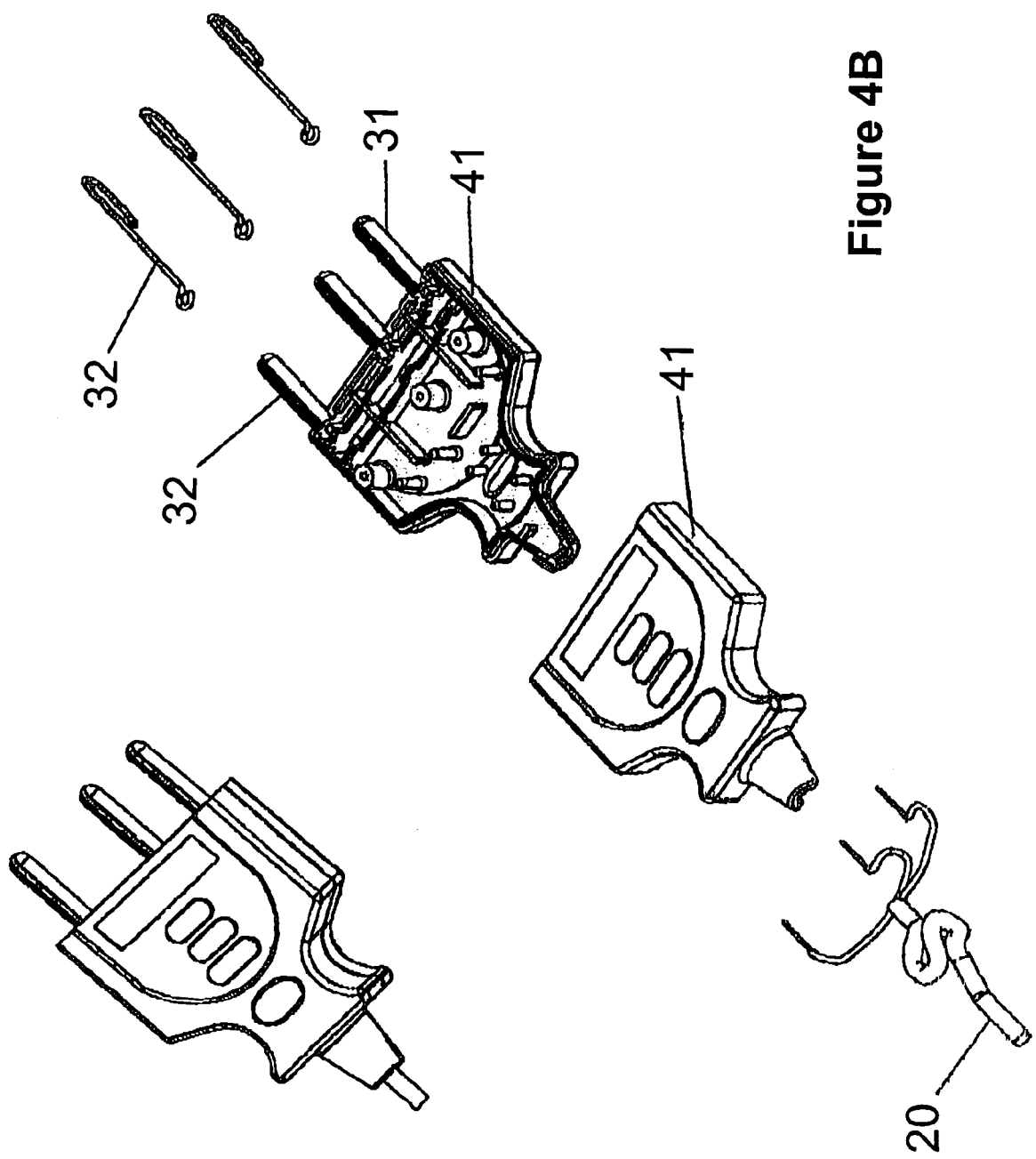
FIG. 4B is a perspective explosive view of another attachment plug of this invention.

FIG. 4B is a perspective explosive view of another attachment plug of this invention. The principal difference between FIG. 4B and FIG. 4A is that no integral inner mould 43 is used in FIG. 4B. The advantage of using an integral mould 43 (in FIG. 4A) resides in its good insulation property. In FIG. 4B, the outer mould 41 is a two-piece construction without the inner mould 43. All part-numbers of FIG. 4B are similar to part-numbers of FIG. 4A except there is no inner mould 43 in FIG. 4B. Constructional spacers and barriers integral with the outer mould 41 are provided so that the three cores avoid contact with each other.

FIG. 5 is a plan with an end view of the cable assembly of this invention. In FIG. 5, since the plug-pins 52 are made of metal, there are two recesses 51 on each side of the plug body which are designed for increasing the flexibility of the plug-pins 52 for easy mating with any loose or tight socket. The recess is a simple notch on the ridge near the plug-pin as shown. The flexibility of the cable is illustrated in FIG. 5B.

While the foregoing description sets forth preferred embodiments of the invention, the foregoing description should not be deemed a limitation of the invention herein. Other adaptations, modifications and alternatives may occur to one skilled in the art without departing from the spirit and scope of the present invention.

What is claimed is:

1. A cable assembly for an electrosurgical pencil comprising a power and signal transmitting multiple-core cable with an attachment plug, in which a power transmitting core has more conductors and thicker insulation than two signal transmitting cores, said attachment plug having either plastic plug-pins with spring-steel strips, or metal plug-pins with recesses on a plug body near the plug-pins to provide flexibility in mating with a socket wherein said attachment plug further comprises a plastic outer mould and an inner mould to prevent said three cores from contact with each other.

2. A cable assembly as in claim 1, wherein said two signal transmitting cores have a reduced diameter in comparison to said power transmitting core.

3. A cable assembly as in claim 1, wherein said inner mould has gutters for embedding said three cores.

4. A cable assembly as in claim 1, wherein said recess is a notch cut on a ridge of the plug body near said plug-pins.

5. A cable assembly as in claim 1, wherein the number of conductors in each signal transmitting core is 4.

6. A cable assembly for an electrosurgical pencil comprising a power and signal transmitting multiple-core cable with an attachment plug, in which a power transmitting core has more conductors and thicker insulation than two signal transmitting cores, said attachment plug having either plastic plug-pins with spring-steel strips, or metal plug-pins with recesses on a plug body near the plug-pins to provide flexibility in mating with a socket, cable assembly as in claim 1, wherein said attachment plug further comprises a plastic outer mould having a two-piece construction without an inner mould and employs constructional spacers and barriers to prevent said three cores from contacting each other.

7. In combination:

an electrosurgical pencil; and a cable assembly for said electrosurgical pencil comprising a power and signal transmitting multiple-core cable with an attachment plug, in which a power transmitting core has more conductors and thicker insulation than two signal transmitting cores, said attachment plug having a pair of plastic plug-pins each with a spring-steel strip to provide flexibility in mating with a socket, wherein said attachment plug further comprises a plastic outer mould and an inner mould to prevent said three cores from contact with each other.

8. A combination as in claim 7, wherein said two signal transmitting cores have a reduced diameter in comparison to said power transmitting core.

9. A combination as in claim 7 wherein said inner mould has gutters for embedding said three cores.

10. A combination as in claim 7, wherein said plug comprises a plug body including a recess configured as a simple notch cut on a ridge of the plug body near said plug-pins.

11. A combination as in claim 7, wherein the number of conductors in each signal transmitting core is 4.

12. In combination:

an electrosurgical pencil; and a cable assembly for an electrosurgical pencil comprising a power and signal transmitting multiple-core cable with an attachment plug, in which a power transmitting core has more conductors and thicker insulation than two signal transmitting cores, said attachment plug having metal plug-pins with recesses on a plug body near the plug-pins to provide flexibility in mating with a socket wherein said attachment plug further comprising a plastic outer mould and an inner mould to prevent said three cores from contact with each other.

13. A combination as in claim 12, wherein said two signal transmitting cores have a reduced diameter in comparison to said power transmitting core.

14. A combination as in claim 12, wherein said inner mould has gutters for embedding said three cores.

15. A combination as in claim 12, wherein each said recess is a notch cut on the ridge of the plug body near the plug-pin.

16. A combination as in claim 12, wherein the number of conductors in each signal transmitting core is 4.

* * * * *

UNITED STATES PATENT AND TRADEMARK OFFICE
CERTIFICATE OF CORRECTION

| | |
|---|---|
| PATENT NO. | : 7,057,111 B2 |
| APPLICATION NO. | : 10/802320 |
| DATED | : June 6, 2006 |
| INVENTOR(S) | : Fung et al. |

It is certified that error appears in the above-identified patent and that said Letters Patent is hereby corrected as shown below:

Column 4:

Lines 6 and 7, delete "cable assembly as in claim 1,"

Line 46, after "socket" insert --,--.

Signed and Sealed this

Twenty-first Day of August, 2007

JON W. DUDAS
*Director of the United States Patent and Trademark Office*